United States Patent [19]

Romeo et al.

[11] Patent Number: 5,300,493

[45] Date of Patent: Apr. 5, 1994

[54] ULCER TREATMENT USING CHOLINE ESTERS OF POLYSACCHARIDES

[75] Inventors: Aurelio Romeo, Rome; Gino Toffano; Lanfranco Callegaro, both of Padova, all of Italy

[73] Assignee: Fidia S.p.A., Abano Terme, Italy

[21] Appl. No.: 945,495

[22] Filed: Sep. 16, 1992

[30] Foreign Application Priority Data

Sep. 16, 1991 [IT] Italy .............. PD91A000163

[51] Int. Cl.$^5$ ................ A61K 31/715; A61K 31/73; A61K 31/045
[52] U.S. Cl. ........................ 514/54; 514/55; 514/57; 514/60; 514/727; 514/925; 514/926
[58] Field of Search .......... 514/54, 55, 57, 60, 514/727, 925, 926

[56] References Cited

U.S. PATENT DOCUMENTS

| | | | |
|---|---|---|---|
| 2,902,479 | 9/1959 | McNeely et al. | 536/3 |
| 4,287,174 | 9/1981 | Laughlin | 424/78 |
| 4,965,353 | 10/1990 | Francesco et al. | 536/55.1 |

FOREIGN PATENT DOCUMENTS

| | | |
|---|---|---|
| 897114 | 10/1983 | Belgium. |
| 0092121 | 10/1983 | European Pat. Off.. |
| 0138572 | 4/1985 | European Pat. Off.. |
| 0206947 | 12/1986 | European Pat. Off.. |
| 0216453 | 4/1987 | European Pat. Off.. |
| 0251905 | 1/1988 | European Pat. Off.. |
| 0342557 | 11/1989 | European Pat. Off.. |
| 1098980 | 1/1968 | United Kingdom. |

OTHER PUBLICATIONS

B. A. McGee et al Clinical Pharmacy, vol. 10 No. 1 (Jan. 1991) pp. 14–25.
CA 60:2201a-W. H. McNeely et al 1960.
E. A. Balazs, Healon, A Guide to its use in Ophthalmic Surgery, ed. D. Miller & R. Stegmann, Chapt. 1, pp. 5–28, 1982.
Fujimori et al. (1987) Journal of Chromatography 414:167–713.

Primary Examiner—Frederick E. Waddell
Assistant Examiner—Gregory Hook
Attorney, Agent, or Firm—Birch, Stewart Kolasch & Birch

[57] ABSTRACT

Acidic polysaccharide esters containing carboxylic groups are useful for protecting against and curing ulcers of the gastro-enteric system. These esters include choline esters with acidic polysaccharide selected from the group consisting of hyaluronic acid, alginic acid, gellan, oxidized cellulose, oxidized chitin, carboxy-hydrocarbyl-cellulose, carboxy-hydrocarbyl-starch and carboxy-hydrocarbyl-chitin, wherein the term hydrocarbyl means the residue of a hydrocarbon selected from the group consisting of by alkyl, aralkyl and cycloalkyl.

30 Claims, No Drawings

ULCER TREATMENT USING CHOLINE ESTERS OF POLYSACCHARIDES

SUMMARY OF THE INVENTION

The present invention is directed to a new use of acidic polysaccharide esters containing carboxylic groups. More precisely, the invention concerns the use of choline esters with acidic polysaccharides selected from the group consisting of hyaluronic acid, alginic acid, gellan, oxidized cellulose, oxidized chitin, carboxy-hydrocarbyl-cellulose, carboxy-hydrocarbyl-starch and carboxy-hydrocarbyl-chitin, wherein hydrocarbyl means the residue of a hydrocarbon selected from the group consisting of alkyl, aralkyl and cycloalkyl. It has been found that these esters are remarkably active in protecting against and curing ulcers of the gastro-enteric system, and that they can therefore be used to advantage in the corresponding therapies.

The esters of said acidic polysaccharides with choline are known and are described in European patent applications Nos. 86305233.8, filed 7 Jul. 1986, 87401464.0, filed 25 Jun. 1987, and 89108628.2, filed 12 May 1989. Their use, as described in these patent applications, comes within the scope of the applications of the esters in general mentioned therein. These include use in the pharmaceutical sector alone, their use in preparations wherein the pharmacological action of the polysaccharide itself is to be exploited, such as in the case of hyaluronic acid in therapy for arthropathies or in ophthalmic surgery, or in preparations in which the esterifying alcoholic component is a substance with a pharmacological activity of its own which is to be exploited and in which therefore the polysaccharide component acts essentially as the vehicle alone. The latter use is exemplified in the case again of hyaluronic esters, hyaluronic acid esters with steroidal alcohols and with alcohols having an antibacterial action. This is also true of the esters of the other acidic polysaccharides mentioned above.

The anti-ulcer properties of the choline esters of said acidic polysaccharides are derived from the polysaccharide component, as the gelling and protective effect of some of said polysaccharides on the mucosa is well known. Such qualities have been described especially for alginic acid and its application is envisaged as a curative agent in gastric inflammation processes.

As another example in the prior art, the sodium salt of an alginic acid derivative comprising a carboxymethyl ether of one of its hydroxy groups, described in U.S. Pat. No. 2,902,479, can be used as an anti-acid agent for the cure of gastric disorders.

It has now been discovered, according to the present invention, that the choline esters with the acidic polysaccharides listed above possess a protective anti-ulcer effect on the gastric mucosa which is very pronounced and greater than that of the known products based on acidic polysaccharides. In the pharmacological experiments reported hereafter, some of the best known protective agents for the gastric mucosa found on the market are also compared to some products of the present invention.

The object of the present invention is therefore the use of a choline ester with a carboxylic acidic polysaccharide or one of its molecular fractions selected from the group consisting of hyaluronic acid, alginic acid, gellan, oxidized cellulose, oxidized chitin, carboxy-hydrocarbyl-cellulose, carboxy-hydrocarbyl-starch and carboxy-hydrocarbyl-chitin, wherein the named hydrocarbyl residue is selected from the group consisting of alkyl, aralkyl and cycloalkyl, as an anti-ulcer and gastroprotective agent.

The esters to be used according to the invention may be total or partial esters, that is, esters wherein all of the carboxy groups are esterified with choline, or respectively, wherein only part of the carboxyls are thus esterified. As a rule, the quaternary ammonium groups in the partial esters are salified with carboxyls which have remained free. Should 50% or less of the carboxy groups of the polysaccharide be esterified, the carboxy groups which are not thus internally salified and which are still free, can be salified in their turn with metals or organic bases, as described hereafter.

The basic polysaccharides mentioned above can have molecular weights varying within suitable limits, like those of the natural materials extracted from plants and animals which contain them, or those which have been chemically or physically modified. Thus, one may use either whole polysaccharides or their molecular fractions. In the present description, the term "acidic polysaccharides" can be taken to mean either the whole acids or their molecular fractions. When choline esters are used with a hyaluronic acid, it is possible to use basic hyaluronic acids extracted from cockscombs and purified according to the methods described in the literature.

Particularly suitable for this use are purified molecular fractions of hyaluronic acid with molecular weights which can vary within wide limits, for example, from about 90–80% to 0.2% of the molecular weight of the whole acid, preferably between 5% and 0.2% by weight. Such fractions can be obtained by various procedures described in the literature, that is, by means of hydrolysis, oxidation or enzymatic procedures or physical procedures, for example, mechanical procedures or by radiation. Accordingly, primordial extracts of the purification process are often formed.

The molecular fractions obtained are separated and purified by known techniques, such as, by molecular filtration. One purified fraction of hyaluronic acid, suitable for use according to the invention, is for example that known as "noninflammatory-NIF-NaHA sodium hyaluronate", described by Balazs in the brochure entitled "Healon—A guide to its use in ophthalmic surgery", D. Miller & Stegmann, eds., John Wiley & Sons, N.Y. 81983, p. 5. Of particular importance as starting materials for the esters of the present invention are two purified fractions obtainable from hyaluronic acid, for example, those extracted from hens' crests, known as "Hyalastine" and "Hyalectin", described in the literature, for example, in EP patent No. 0138572. The fraction "Hyalastine" has a mean molecular weight of about 50,000 to 100,000, while the fraction "Hyalectin" has a mean molecular weight of about 500,000 to 730,000. Another fraction has been isolated which is a combination of these two, and it has been characterized as having a mean molecular weight of about 250,000 to 350,000. This combined fraction can be obtained with a yield of 80% of the total hyaluronic acid available from the particular starting material, while the fraction "Hyalectin" can be obtained with a yield of 30%, and the fraction "Hyalastine" with a yield of 50%, of the starting hyaluronic acid.

The alginic acid used in the preparation of choline esters can be of various origins and can have a variety of molecular weights. The degree of polymerization of this polysaccharide, formed from D-mannuronic and L-glucuronic acid, varies according to the kind of algae used for its extraction (for example Phaecophyceae), the time of year, the place where it was gathered, and the age of the plant. Alginic acid can also be obtained by microbiological means, for example, by fermentation with *Pseudomonas aeruoinosa* or mutants of *Pseudomonas putida, Pseudomonas fluorescens* and *Pseudomonas mendocina*. For the preparation of choline esters according to the present invention, alginic acids of either low molecular weight of about 20,000, or high molecular weight of about 400,000 are preferred.

The non-acidic, basic polysaccharides used for the preparation of said acidic polysaccharides containing the carboxy group (cellulose or chitin oxidate) or the hydrocarbyl carboxy group can also have molecular weights which vary within wide limits, such as especially native materials extracted from plants and animals, or those modified by chemical-physical action. Cellulose, for example, can be native cellulose from cotton with about 3,000 units of D-glucose, or regenerated, for example mercerized cellulose, or cellulose degraded for example by the action of mineral acids or enzymes. The starch can come from any type of plant, for example potatoes or cereals, and therefore may contain variable quantities of the two ordinary starch components, amylose and amylopectin. It is also possible to use starches mainly containing, for example, amylopectin, such as those derived from certain types of wheat, sorghum, oats or rice, and it is possible to use also the 2-amylose and amylopectin fractions obtained by separation according to known methods. Finally, it is also possible to use partially hydrolyzed starches as a starting material.

The chitin used in the preparation of oxidized chitin or carboxy-hydrocarbyl-chitin, to be used in turn in the preparation of choline esters according to the invention, is for example that extracted from fungi or algae. Derivatives thereof obtained by partial hydrolysis can also be used.

Among all of these polysaccharides, it is preferable to use the commercially available products.

In the aforesaid carboxy-hydrocarbyl-derivatives of cellulose, starch and chitin, the hydrocarbyl group is chosen from alkyl, aralkyl and cycloalkyl. Alkyl is above all a lower alkyl, especially a straight-chained alkyl, with a maximum of 6 carbon atoms. Alkyl is preferably a methyl group. Aralkyl is preferably a group derived from a pure alkyl having a maximum of 6 carbon atoms, especially methyl, and in which the aryl group is a benzene residue, unsubstituted or substituted by 1–3 lower alkyl groups having a maximum of 4 carbon atoms, especially methyl or hydroxy, or alkoxy groups having a maximum of 4 carbon atoms. A cycloalkyl group is preferably a group with a maximum of 6 carbon atoms in the ring, especially between 3 and 6 atoms, which can be substituted by 1 to 3 lower alkyl groups, especially methyl groups.

The partial esters of choline with the aforesaid acidic polysaccharides can also be used as inner salts obtained directly by esterification or in the form of their metal salts or therapeutically acceptable organic bases. This use constitutes a preferential object of the present invention. Of particular importance are the salts of alkali or alkaline earth metals, such as in particular sodium, potassium, ammonium, calcium or magnesium salts.

The therapeutically acceptable organic bases for the preparation of salts to be used according to the invention should preferably be free from pharmacological activity of their own, while not excluding pharmacologically active bases with an action which is compatible with the intended antiulcer and gastroprotective use. Such bases include bases having a spasmolytic action or antagonists of histamine $H_2$-receptors such as cimetidine, ranitidine or ticlopidine. Examples of pharmacologically inert bases are aliphatic amines, for example mono-, di-, and trialkylamines with alkyl groups having a maximum of 6 carbon atoms, or arylalkylamines with the same number of carbon atoms in the aliphatic part or where aryl means a benzene group, optionally substituted by 1 to 3 methyl groups, halogen atoms, hydroxy groups or alkoxy groups such as methoxy groups. The bases can be cyclic, such as monocyclic alkylene amines with rings of 4 to 6 carbon atoms, optionally interrupted in the carbon atom chain by heteroatoms selected from the group consisting of oxygen, nitrogen and sulfur, such as piperidine or morpholine. The bases can also be substituted by amino or hydroxy functions, such as aminoethanol or choline itself. Quaternary ammonium salts of these basic groups can also be formed, such as tetraalkylammonium salts, for example, tetramethylammonium or higher homologues, such as those having a maximum of 4 carbon atoms in the alkyl groups.

The superior gastroprotective activity of the choline esters with the aforesaid acidic polysaccharides according to the present invention has been demonstrated by pharmacological experiments performed on two esters of an alginic acid with choline, being thus identified:

Alau 0101—p.40=alginic acid ester with a molecular weight of 200,000 with choline as described in Example 5

Alau 0801—p.40=alginic acid ester with a molecular weight of 70,000 with choline as described in Example 6 and on commercially available gastroprotective products, and more exactly with:

sucralfate=octasulfonic saccharose ester aluminum salt

Maalox TC=aluminum and magnesium hydroxides

Gaviscon=sodium alginate, sodium bicarbonate and on alginic acid itself.

1. Gastric lesions induced by reserpine

Description of the Model

The study was performed on male Sprague-Dawley rats (170–190 g): housed in metabolic cages and denied food for 48 hours before the tests (but with free access to water).

The test products were administered orally (gastric tube) twice, immediately before reserpine injection and two hours later, at doses of 200–400 mg/kg in 15 ml/kg of distilled water.

The following products were tested:
Alau 0101
Alau 0801
sucralfate
alginic acid

The controls were kept under the same experimental conditions and received 15 ml/kg of physiological saline solution.

Reserpine was injected i.p. at a dose of 20 mg/kg (in 10 ml/kg of a 0.5% solution of acetic acid). The animals were sacrificed 4 hours later and their stomachs removed and opened along the greater curvature, washed with saline solution, fixed into position and observed under a magnifying glass.

Parameters

The gastric lesions were assessed in two ways:
a) on the basis of the number of ulcers present in the mucosa (regardless of their dimensions).
b) on the basis of a score of gastrolesions according to the following scale:
0 = no lesions
0.5 = widespread hyperemia
1 = 1-2 punctate ulcers
2 = 3-10 punctate ulcers
3 = >10 punctate ulcers and/or 1 large ulcer
4 = 2 or more large ulcers, or 1 or more perforating ulcers

Results

The results obtained (Table 1) indicate that:
Alau 0101 and Alau 0801 have a marked gastroprotective activity. The effect is dose-dependent and evident at as low a dose as 200 mg/kg os (the percentage of protection with regard to the number of ulcers present in the mucosa of controls treated with saline was 54% and 51% respectively), reaching maximum activity at a dose of 400 mg/kg os (percentage of protection was 94% and 90% respectively);
the efficacy of Alau 0101 and Alau 0801 is greater than that of sucralfate (26% of protection at 400 mg/kg), while alginic acid alone is ineffective.

It can therefore be concluded that both Alau derivatives have a marked protective activity in a model in which the ulcerogenic effect of reserpine is essentially correlated with the release of serotonin from the mast cells.

TABLE 1

Effect of Alau 0101 and Alau 0801 (vs sucralfate and alginic acid) on gastric lesions induced by reserpine

| Group (No) | Treatment os | dose mg/kg × 2 | mean No. ulcers per rat ± S.E. | mean gastric lesions ± S.E. |
|---|---|---|---|---|
| I (30) | Saline | 15 ml/kg | 12.60 ± 0.89 (—) | 4.00 ± 0.00 (—) |
| II (10) | ALAU 0101 | 200 | 5.80 ± 0.55 (54%) | 2.80 ± 0.13 (30%) |
| III (10) | ALAU 0101 | 400 | 0.80 ± 0.20 (94%) | 0.70 ± 0.18 (82%) |
| IV (10) | ALAU 0801 | 200 | 6.20 ± 0.61 (51%) | 3.00 ± 0.15 (25%) |
| V (10) | ALAU 0801 | 400 | 1.20 ± 0.33 (90%) | 0.80 ± 0.15 (80%) |
| VI (10) | sucralfate | 400 | 9.30 ± 1.12 (26%) | 2.80 ± 0.29 (30%) |
| VII (10) | alginic acid | 400 | 12.30 ± 1.71 (2%) | 4.00 ± 0.00 (—) |

No. corresponds to the number of animals per group
In parentheses the percentage of protection compared to controls treated with saline

2. Gastric lesions induced by serotonin

Description of the Model

The study was performed on male Sprague-Dawley rats (150-160 g) housed in metabolic cages and denied food for 48 hrs before the tests (but with free access to water).

The test products (Alau 0101—sucralfate—Maalox) were tested orally (gastric tube) under three different sets of experimental conditions:
1) twofold oral administration (400 mg/kg) immediately before serotonin injection and 2 hrs later.
2) single oral administration (400 mg/kg) immediately before serotonin injection.
3) single oral administration (400 mg/kg) 2 hrs after serotonin administration.

Under the same experimental conditions, the controls received 15 ml/kg of physiological saline solution. The serotonin creatine sulfate was injected s.c. at a dose of 35 mg/kg. The animals were sacrificed 4 hrs later and their stomachs removed and opened along the greater curvature, washed with saline fixed into position and observed under a magnifying glass.

Parameters

The gastric lesions were assessed in 2 different ways:
a) on the basis of the number of ulcers present in the mucosa (regardless of their dimensions).
b) on the basis of a score according to the following scale:
0 = no lesions
0.5 = widespread hyperemia
1 = 1-2 punctate ulcers
2 = 3-10 punctate ulcers
3 = punctate necrosis and/or 1 large ulcer
4 = 2 or more large ulcers, or 1 or more perforating ulcers

Results

The results obtained (Table 2) indicate that:
Alau 0101 has a gastroprotective activity (91% of protection, after two administrations of 400 mg/kg os, with regard to the number of ulcers present in the mucosa of the saline-treated controls)
the effect of Alau is evident even after 1 single administration before ("preventive effect") inducement of the gastric lesion (about 69% protection), while it is less marked (45% protection) when not administered until after the lesion ("curative effect")
the efficacy of Alau is greater than that of sucralfate (43% protection at two doses of 400 mg/kg each), and equal to that of Maalox.

It can therefore be concluded that Alau 0101 has a valid gastroprotective activity in experimental conditions of gastric lesions induced by serotonin. The data also weigh in favor of an essentially preventive and only partially curative effect.

TABLE 2

Effect of Alau 0101 (vs sucralfate and Maalox) on gastric lesions induced by serotonin

| Group (No.) | Treatment os | Dose | Equiv. STD* | Mean No. ulcers per rat ± S.E. | Mean gastric lesions ± S.E. |
|---|---|---|---|---|---|
| I (30) | Saline | 15 ml/kg | | 15.00 ± 1.23 (—) | 3.90 ± 0.06 (—) |
| II (10) | ALAU 0101 | 400 (mg/kg) × 2 | 24 | 1.30 ± 0.37 (91%) | 0.75 ± 0.17 (81%) |
| III (10) | Sucralfate | 400 (mg/kg) × 2 | 24 | 8.50 ± 0.98 (43%) | 2.40 ± 0.27 (39%) |

TABLE 2-continued

Effect of Alau 0101 (vs sucralfate and Maalox) on gastric lesions induced by serotonin

| Group (No.) | Treatment os | Dose | Equiv. STD* | Mean No. ulcers per rat ± S.E. | Mean gastric lesions ± S.E. |
| --- | --- | --- | --- | --- | --- |
| IV (10) | Maalox TC | 6.0 (ml/kg) × 2 | 24 | 1.20 ± 0.36 (92%) | 0.70 ± 0.18 (82%) |
| V (10) | ALAU 0101 | 400 mg/kg** | | 4.60 ± 0.72 (69%) | 1.55 ± 0.24 (60%) |
| VI (10) | ALAU 0101 | 400 mg/kg*** | | 8.20 ± 1.10 (45%) | 2.40 ± 0.22 (39%) |

No. corresponds to the number of animals per group
In parentheses the percentage of protection compared to saline-treated controls
*Dose expressed in equivalent STD, corresponding to the single dose indicated in therapy
**Alau in a single dose before lesion
***Alau in a single dose 2 hrs after lesion 3. Gastric lesions induced by ethyl alcohol Description of the Model The study was performed on male Sprague-Dawley rats (180–200 g): housed in metabolic cages and fed with a 5% glucose solution alone +0.4% NaCl, but denied all other food for 48 hours before the tests. The test products (Alau 0101—sucralfate—Maalox—Gaviscon) were administered orally (at doses of between 200–400 mg/kg) by means of a gatric tube, in 15 ml/kg of saline solution.

Ten minutes after treatment, 1.5 ml/rat of absolute ethyl alcohol were administered. The animals were sacrificed 1 hr later. Their stomachs were removed, opened along the greater curvature, washed with saline solution, fixed in position and observed under a magnifying glass.

Parameters

The gastric lesions were assessed according to the following scale (from 0 to 5):
0 = no lesions
1 = widespread hyperemia
1.5 = 1 hemorrhagic zone
2 = hemorrhagic zones
2.5 = 1-2 hemorrhagic zones + punctate lesions
3 = 3-4 hemorrhagic zones
5 hemorrhagic zones (or 3 hemorrhagic zones punctate lesions
4.5 = 4-5 hemorrhagic zones + punctate lesions
5 = 6 or more hemorrhagic zones (or 5 hemorrhagic zones + punctate lesions)

The mean gastric lesion rating was therefore indicated on the basis of said scale.

Results

The results obtained (Table 3) indicate that:
Alau 0101 has an appreciable gastroprotective activity at a dose of 400 mg/kg (50% of protection compared to saline-treated controls)
the gastroprotective efficacy of Alau 0101 is greater than that of Gaviscon and sucralfate, while it is comparable to that of Maalox.

TABLE 3

Effect of Alau 010 (vs sucralfate and Maalox) on gastric lesions induced by ethyl alcohol

| Group (No.) | Treatment os | Dose | Equivalent STD* | Mean gastric lesions ± S.E. |
| --- | --- | --- | --- | --- |
| I (20) | Saline | — | — | 4.85 ± 0.08 (—) |
| II (10) | Alau 0101 | 200 mg/kg | 12 | 3.60 ± 0.22 (26%) |
| III (10) | Alau 0101 | 400 mg/kg | 24 | 2.45 ± 0.17 (50%) |
| IV (10) | Sucralfate | 200 mg/kg | 12 | 4.30 ± 0.11 (11%) |
| V (10) | Sucralfate | 400 mg/kg | 24 | 2.95 ± 0.14 (39%) |
| VI (10) | Maalox TC | 5 ml/kg | 20 | 2.85 ± 0.15 (41%) |
| VII (10) | Gaviscon | 2.0 ml/kg 4.0 ml/kg | 10 | 4.35 ± 0.18 (10%) |
| VIII (10) | Gaviscon | | 20 | 3.25 ± 0.21 (33%) |

*Dose expressed as STD equivalent corresponding to the single dose indicated in therapy
No. corresponds to the number of animals per group
In parentheses the percentage of protection compared to saline-treated controls The aforesaid results show that the alginic esters of choline have a valuable gastroprotective activity. In particular, it is interesting to emphasize that:
Alau 0101 and Alau 0801 have a marked gastroprotective activity, especially on gastric lesions induced by reserpine and serotonin:
The effect is dose-dependent with maximum efficacy after two administrations of 400 mg/kg/os (maximum protection value of 94%)
The effect is mainly preventive and only partly curative. Indeed, a notable gastroprotective activity was observed (69%) even after 1 single administration, before inducement of the gastric lesion.
The gastroprotective efficacy of Alau 0101 and Alau 0801 is greater than that of sucralfate and Gaviscon (as shown particularly in the aforecited models of gastric lesions and in gastric lesions induced by ethanol) and comparable to that of Maalox (as shown in lesions induced by ethanol and reserpine, respectively). Alginic acid alone is not effective.
It is also interesting to observe that the notable gastroprotective activity of the choline esters is fundamentally evident in two models, in which serotonin is directly or indirectly involved. Serotonin has a strong action on the gastric secretion of acids, through its effect on histamine.

The present invention also includes pharmaceutical preparations for oral administration, containing a choline ester with said acidic polysaccharides or one of the aforesaid salts of partial esters, in particular those especially mentioned, optionally together with excipients suitable for this form of administration, such as pills, tablets, gelatin capsules, capsules, or as solutions or freeze-dried powders or granules. They contain preferably between 10% and 100% by weight of active compound. Preferred examples of such excipients are in particular anti-acid substances of a basic nature, such as basic magnesium or calcium salts. The excipients can themselves constitute a layer of the tablets or other forms of pharmaceutical preparations to be used according to the invention. The esters to be used according to the present procedures, for example, those described in one of the previously cited European patents for the preparation of esters in general and their salts.

The invention is illustrated by the following Examples:

EXAMPLE 1

PREPARATION OF THE PARTIAL ESTER OF ALGINIC ACID WITH CHOLINE (5% of the carboxyls esterified)

4.17 g (10 mEq) of the tetrabutylammonium salt of alginic acid, with a molecular weight of 200,000 are solubilized in 160 ml of a mixture of $NMP/H_2O$ 95:5. The solution is cooled to 0° C. and to it is added 0.124 g (0.5 mEq) of (2-bromoethyl)trimethylammonium bromide, finely ground and suspended in 10 ml of pure NMP. The suspension is added slowly over 30 minutes, while being constantly stirred. After 2 hours the resulting mixture is heated to 30° C. and stirred for 14 hours. To the reaction mixture are added 320 ml of ethyl acetate. The precipitate thus formed is separated by filtration, washed twice with 50 ml of ethyl acetate and then vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester named in the heading, is separated by filtration, washed twice with 50 ml of 95% ethanol and once with 50 ml of acetone and lastly vacuum-dried. Yield = 1.9 g.

Quantitative determination of the choline, performed according to the method of Kannosuke Fujimori et al. (J. Chromatography 414, 167 [1987]) after alkaline hydrolysis of the product in 0.1N NaOH at 45° C. for 30 minutes, shows a choline content of 0.24 mEq/g.

EXAMPLE 2

PREPARATION OF THE PARTIAL ESTER OF ALGINIC ACID WITH CHOLINE (10% of the carboxyls esterified)

4.17 g (10 mEq) of the tetrabutylammonium salt of alginic acid, with a molecular weight of 200,000, are solubilized in 160 ml of a mixture of NMP/H20 95:5. The solution is cooled to 0° C. and to it are added 0.247 g (1.0 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 1.95 g.

Quantitative determination of the choline, performed according to the method of Kannosuke Fujimori et al. (J. Chromatography 414, 167 [1987]) after the product has undergone alkaline hydrolysis in 0.1N NaOH at 45° C. for 30 minutes, shows a choline content of 0.48 mEq/g.

EXAMPLE 3

PREPARATION OF THE PARTIAL ESTER OF ALGINIC ACID WITH CHOLINE (20% of the carboxyls esterified)

4.17 g (10 mEq) of the tetrabutylammonium salt of alginic acid, with a molecular weight of 200,000, are solubilized in 160 ml of a mixture of $NMP/H_2O$ 95:5. The solution is cooled to 0° C. and to it is added 0.494 g (2.0 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 2.01 g.

Quantitative determination of the choline, performed according to the method of Kannosuke Fujimori et al. (J. Chromatography 414, 167 [1987]) after the product has undergone alkaline hydrolysis in NaOH 0.1N at 45° C. per 30 minutes, shows a choline content of 0.95 mEq/g.

EXAMPLE 4

PREPARATION OF THE PARTIAL ESTER OF ALGINIC ACID WITH CHOLINE (30% of the carboxyls esterified)

4.17 g (10 mEq) of the tetrabutylammonium salt of alginic acid, with a molecular weight of 200,000, are solubilized in 160 ml of a mixture of $NMP/H_2O$ 95:5. The solution is cooled to 0° C. and to it is added 0.741 g (3.0 mEq) of (2-bromoethyl)trimethylammonium bromide finely ground and suspended in 10 ml of pure NMP. The suspension is slowly added over 30 minutes while being constantly stirred. 2 hours later the resulting mixture is cooled to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 2.05 g.

Quantitative determination of the choline, performed according to the procedure Kannosuke Fujimori et al. (J. Chromatography 414, 167 [1987]) after the product has undergone alkaline hydrolysis in NaOH 0.1N at 45° C. for 30 minutes, shows a choline content of 1.40 mEq/g.

EXAMPLE 5

PREPARATION OF THE PARTIAL ESTER OF ALGINIC ACID WITH CHOLINE (40% of the carboxyls esterified)

4.17 g (10 mEq) of the tetrabutylammonium salt of alginic acid, with a molecular weight of 200,000, are solubilized in 160 ml of a mixture of NMP/$H_2O$ 95:5. The solution is cooled to 0° C. and to it is added 1.087 g (4.4 mEq) of (2-bromoethyl)trimethylammonium bromide finely ground and suspended in 10 ml of pure NMP. The suspension is slowly added over 30 minutes while being stirred. After 2 hours the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield=2.03 g.

Quantitative determination of the choline, performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 1.85 mEq/g.

EXAMPLE 6

PREPARATION OF THE PARTIAL ESTER OF ALGINIC ACID WITH CHOLINE (40% of the carboxyls esterified)

4.17 g (10 mEq) of the tetrabutylammonium salt of alginic acid, with a molecular weight of 200,000 and having a high mannuronic content, are solubilized in 160 ml of a mixture of NMP/$H_2O$ 95:5. The solution is cooled to 0° C. and to it are added 1.087 g (4.4 mEq) of (2-bromoethyl)trimethylammonium bromide finely ground and suspended in 10 ml of pure NMP. The suspension is slowly added over 30 minutes while being constantly stirred. After 2 hours the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield=2.03 g.

Quantitative determination of the choline performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 1.85 mEq/g.

EXAMPLE 7

PREPARATION OF THE PARTIAL ESTER OF ALGINIC ACID WITH CHOLINE (40% of the carboxyls esterified)

4.17 g (10 mEq) of the tetrabutylammonium salt of alginic acid, with a molecular weight of 70,000, are solubilized in 160 ml of a mixture of NMP/$H_2O$ 95:5. The solution is cooled to 0° C. and to it are added 1.087 g (4.4 mEq) of (2-bromoethyl)trimethylammonium bromide finely ground and suspended in 10 ml of pure NMP. The suspension is slowly added over 30 minutes while being constantly stirred. After 2 hours the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and then precipitated by adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield=2.03 g.

Quantitative determination of the choline, performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 1.85 mEq/g.

EXAMPLE 8

PREPARATION OF THE PARTIAL ESTER OF A CARBOXYMETHYLCELLULOSE WITH CHOLINE (30% of the carboxyls esterified)

4.62 g (10 mEq) of the tetrabutylammonium salt of a carboxymethylcellulose with a degree of substitution =1.0, are solubilized in 160 ml of a mixture of NMP/$H_2O$ 95:5. The solution is cooled to 0° C. and to it are added 0.71 g (3.0 mEq) of (2-bromoethyl)trimethylammonium bromide finely ground and suspended in 10 ml of pure NMP. The suspension is slowly added over 30 minutes while stirring. After 2 hours the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of $H_2O$ containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield=2.50 g.

Quantitative determination of the choline, performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 1.16 mEq/g.

EXAMPLE 9

PREPARATION OF THE PARTIAL ESTER OF A CARBOXYMETHYLCELLULOSE WITH CHOLINE (40% of the carboxyls esterified)

4.62 g (10 mEq) of the tetrabutylammonium salt of a carboxymethylcellulose having a degree of substitution=1.0, are solubilized in 160 ml of a mixture of NMP/$H_2O$ 95:5. The solution is cooled to 0° C. and to it are added 1.09 g (4.4 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of H$_2$O containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 2.80 g.

Quantitative determination of the choline, performed according to the procedure Kannosuke Fujimori et al. (J. Chromatography 414, 167 [1987]) after the product has undergone alkaline hydrolysis in NaOH 0.1N at 45° C. for 30 minutes, shows a choline content of 1.38 mEq/g.

EXAMPLE 10

PREPARATION OF A PARTIAL ESTER OF A CARBOXYMETHYLCELLULOSE WITH CHOLINE (30% of the carboxyls esterified)

5.16 g (10 mEq) of the tetrabutylammonium salt of a carboxymethylcellulose having a degree of substitution=0.75, are solubilized in 160 ml of a mixture of NMP/H$_2$O 95:5. The solution is cooled to 0° C. and to it is added 0.71 g (3.0 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of H$_2$O containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 3.02 g.

Quantitative determination of the choline, performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 0.96 mEq/g.

EXAMPLE 11

PREPARATION OF A PARTIAL ESTER OF A CARBOXYMETHYLCELLULOSE WITH CHOLINE (40% of the carboxyls esterified)

5.16 g (10 mEq) of the tetrabutylammonium salt of a carboxymethylcellulose with a degree of substitution =0.75, are solubilized in 160 ml of a mixture of NMP/H$_2$O 95:5. The solution is cooled to 0° C. and to it are added 1.087 g (4.4 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of H$_2$O containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 3.06 g.

Quantitative determination of the choline, performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 1.25 mEq/g.

EXAMPLE 12

PREPARATION OF THE PARTIAL ESTER OF A HYALURONIC ACID WITH CHOLINE (30% of the carboxyls esterified)

6.21 g (10 mEq) of the tetrabutylammonium salt of hyaluronic acid are solubilized in 160 ml of a mixture of NMP/H$_2$O 95:5. The solution is cooled to 0° C. and to it is added 0.710 g (3.0 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of H$_2$O containing 1.5 g of NaCl at 4° C. The solution is filtered and precipitated by slowly adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 4.03 g.

Quantitative determination of the choline, performed according to the procedure of Kannosuke Fujimori et al. (J. Chromatography 414, 167 [1987]) after the product has undergone alkaline hydrolysis in NaOH 0.1N at 45° C. for 30 minutes, shows a choline content of 0.71 mEq/g.

EXAMPLE 13

PREPARATION OF THE PARTIAL ESTER OF A HYALURONIC ACID WITH CHOLINE (40% of the carboxyls esterified)

6.21 g (10 mEq) of the tetrabutylammonium salt of hyaluronic acid are solubilized in 160 ml of a mixture of NMP/H$_2$O 95:5. The solution is cooled to 0° C. and it is added 1.087 g (4.4 mEq) of (2-bromoethyl)trimethylammonium bromide finely ground and suspended in 10 ml of pure NMP. The suspension is slowly added over 30 minutes while being constantly stirred. 2 hours later the resulting mixture is heated to 30° C. and stirred for 14 hours. To the reaction mixture are added 320 ml of ethyl acetate. The precipitate thus formed is separated by filtration, washed twice with 50 ml of ethyl acetate and finally vacuum-dried. The solid matter is solubilized in 150 ml of H$_2$O containing 1.5 g of NaCl at 4° C. The solution is filtered and then precipitated by adding 450 ml of 95% ethanol while stirring. The precipitate, which constitutes the ester defined in the heading, is separated by filtration, washed twice with 50 ml of 95% ethanol and once with 50 ml of acetone and finally vacuum-dried. Yield = 4.05 g.

Quantitative determination of the choline, performed according to the procedure of Kannosuke Fujimori et al. (J Chromatography 414, 167 [1987]) after the product has undergone alkaline hydrolysis in NaOH 0.1N at 45° C. for 30 minutes, shows a choline content of 0.932 mEq/g.

EXAMPLE 14

Pharmaceutical preparations in packets containing granules to mix with water before use.

| Preparation No. 1: a packet containing granules which contains: | |
|---|---|
| active principle | 400 mg |
| excipients: | |
| cross-linked sodium carboxymethylcellulose | 450 mg |
| colloidal silica | 10 mg |
| talc | 30 mg |
| aspartame | 20 mg |
| natural flavoring | q.b. |
| sucrose | q.s. to 3.500 |
| Preparation No. 2: a packet containing granules, which contains: | |
| active principle | 800 mg |
| excipients: | |
| cross-linked sodium carboxymethylcellulose | 900 mg |
| colloidal silica | 20 mg |
| talc | 60 mg |
| aspartame | 40 mg |
| natural flavoring | q.b. |
| sucrose | q.s. to 7.000 |
| Preparation No. 3: a packet containing granules, which contains: | |
| active principle | 400 mg |
| excipients: | |
| sodium carboxymethyl starch | 400 mg |
| colloidal silica | 20 mg |
| talc | 30 mg |
| aspartame | 10 mg |
| natural flavoring | q.b. |
| fructose | q.s. to 2.500 |
| Preparation No. 4: a packet containing granules, which contains: | |
| active principle | 800 mg |
| excipients: | |
| sodium carboxymethyl starch | 800 mg |
| colloidal silica | 40 mg |
| talc | 60 mg |
| aspartame | 20 mg |
| natural flavoring | q.b. |
| fructose | q.s. to 5.000 |
| Preparation No. 5: a packet containing granules, which contains: | |
| active principle | 400 mg |
| excipients: | |
| corn starch | 700 mg |
| talc | 30 mg |
| magnesium stearate | 10 mg |
| colloidal silica | 10 mg |
| aspartame | 20 mg |
| natural flavoring | q.b. |
| sucrose | q.s. to 3.500 |
| Preparation No. 6: a packet containing granules, which contains: | |
| active principle | 800 mg |
| excipients: | |
| corn starch | 1.400 mg |
| talc | 60 mg |
| magnesium stearate | 20 mg |
| colloidal silica | 20 mg |
| aspartame | 40 mg |
| natural flavoring | q.b. |
| sucrose | q.s. to 7.000 |
| Preparation No. 7: a packet containing granules, which contains: | |
| active principle | 400 mg |
| excipients: | |
| cross-linked polyvinylpyrrolidone | 700 mg |
| talc | 30 mg |
| magnesium stearate | 10 mg |
| colloidal silica | 10 mg |
| aspartame | 10 mg |
| natural flavoring | q.b. |
| fructose | q.s. to 2.500 |
| Preparation No. 8: a packet containing granules, which contains: | |
| active principle | 800 mg |
| excipients: | |
| cross-linked polyvinylpyrrolidone | 1.400 mg |
| talc | 60 mg |
| magnesium stearate | 20 mg |
| colloidal silica | 20 mg |
| aspartame | 20 mg |
| natural flavoring | q.b. |
| fructose | q.s. to 5.000 |
| Preparation No. 9: a packet containing granules, which contains: | |
| active principle | 400 mg |
| excipients: | |
| microcrystalline cellulose | 500 mg |
| sodium carboxymethylcellulose | 200 mg |
| mannitol | 200 mg |
| colloidal silica | 10 mg |
| aspartame | 10 mg |
| natural flavoring | q.b. |
| fructose | q.s. to 2.500 |
| Preparation No. 10: a packet containing granules, which contains: | |
| active principle | 800 mg |
| excipients: | |
| microcrystalline cellulose | 1.000 mg |
| sodium carboxymethylcellulose | 400 mg |
| mannitol | 400 mg |
| colloidal silica | 20 mg |
| aspartame | 20 mg |
| natural flavoring | q.b. |
| fructose | q.s. to 5.000 |

EXAMPLE 15

Pharmaceutical preparations in tablet form to be dissolved in the mouth.

| Preparation No. 1: one tablet contains: | |
|---|---|
| active principle | 400 mg |
| excipients: | |
| sodium carboxymethyl starch | 100 mg |
| colloidal silica | 10 mg |
| talc | 30 mg |
| magnesium stearate | 10 mg |
| natural flavoring | q.b. |
| sucrose | q.s. to 1.300 |
| Preparation No. 2: one tablet contains: | |
| active principle | 400 mg |
| excipients: | |
| corn starch | 200 mg |
| colloidal silica | 10 mg |
| talc | 30 mg |
| magnesium stearate | 10 mg |
| natural flavoring | q.b. |
| sucrose | q.s. to 1.300 |
| Preparation No. 3: one tablet contains: | |
| active principle | 400 mg |
| excipients: | |
| microcrystalline cellulose | 300 mg |
| talc | 20 mg |
| magnesium stearate | 10 mg |
| natural flavoring | q.b. |
| aspartame | q.b. |
| sucrose | q.s. to 1.300 |
| Preparation No. 4: one tablet contains: | |
| active principle | 400 mg |
| excipients: | |
| lactose | 250 mg |
| talc | 20 mg |
| magnesium stearate | 10 mg |
| aspartame | q.b. |
| natural flavoring | q.b. |
| sucrose | q.s. to 1.300 |
| Preparation No. 5: one tablet contains: | |
| active principle | 400 mg |
| excipients: | |
| cross-linked polyvinylpyrrolidone | 300 mg |
| colloidal silica | 20 mg |
| talc | 20 mg |
| magnesium stearate | 10 mg |

| | |
|---|---|
| natural flavoring | q.b. |
| sucrose | q.s. to 1.300 |
| Preparation No. 6: one tablet contains: | |
| active principle | 400 mg |
| excipients: | |
| sodium carboxymethyl starch | 200 mg |
| talc | 30 mg |
| magnesium stearate | 10 mg |
| corn starch | 200 mg |
| natural flavoring | q.b. |
| aspartame | q.b. |
| microcrystalline cellulose | q.s. to 1.300 |

The following is claimed:

1. A method for preventing or treating gastric ulcers, which comprises orally administering to a patient in need thereof an effective gastroprotective and anti-ulcer amount of a pharmaceutical composition comprising a choline ester of an acidic polysaccharide selected from the group consisting of hyaluronic acid, alginic acid, gellan, oxidized cellulose, oxidized chitin, carboxy-hydrocarbyl-cellulose, carboxy-hydrocarbyl-starch and carboxy-hydrocarbyl-chitin, in which the hydrocarbyl is the residue of an alkyl, aralkyl or cycloalkyl group, or a metal or organic base salt thereof, and a pharmaceutically acceptable excipient or carrier.

2. The method according to claim 1, wherein the alkyl group is straight-chained and has a maximum of 6 carbon atoms.

3. The method according to claim 2, wherein the alkyl group is methyl.

4. The method according to claim 1, wherein the aralkyl group has a maximum of 6 carbon atoms in the alkyl part and wherein the aryl group is a benzene residue, unsubstituted or substituted by 1-3 lower alkyl or alkoxy groups having a maximum of 4 carbon atoms.

5. The method according to claim 4, wherein the alkyl groups are methyl groups.

6. The method according to claim 1, wherein the cycloalkyl group has a maximum of 6 carbon atoms in the ring, and is optionally substituted by 1-3 methyl groups.

7. The method according to claim 1, wherein the polysaccharide is purified hyaluronic acid extracted from cockscombs.

8. The method according to claim 1, wherein molecular fractions of hyaluronic acid with molecular weights varying between 90% and 0.2% of the molecular weight of the whole acid are used as starting acidic polysaccharides.

9. The method according to claim 8, wherein the polysaccharide is the commercially available product known as "non-inflammatory sodium hyaluronate-NIF-NaHA".

10. The method according to claim 8, wherein the polysaccharide is a hyaluronic acid fraction having a mean molecular weight between 50,000 and 100,000.

11. The method according to claim 8, wherein the polysaccharide is a hyaluronic acid fraction having a mean molecular weight of between 500,000 and about 730,000.

12. The method according to claim 8, wherein the polysaccharide is a hyaluronic acid fraction having a mean molecular weight of between about 250,000 and about 350,000.

13. The method according to claim 1, wherein the polysaccharide is high-molecular-weight alginic acid.

14. The method according to claim 1, wherein the polysaccharide is low-molecular-weight alginic acid.

15. The method according to claim 1, wherein the polysaccharide is gellan.

16. The method according to claim 1, wherein the polysaccharide is oxidized cellulose or basic carboxyalkyl-cellulose derived from native cotton cellulose with about 3,000 units of glucose.

17. The method according to claim 1, wherein the polysaccharide is oxidized cellulose or basic alkyl-cellulose derived from mercerized or regenerated or degraded cellulose.

18. The method according to claim 1, wherein basic carboxyalkyl-starches derived from starches with varying contents of amylose and amylopectin are used as the starting polysaccharide.

19. The method according to claim 1, wherein basic carboxyalkyl-starches derived from starches constituted mainly by amylopectin are used as the starting polysaccharide.

20. The method according to claim 1, wherein basic carboxyalkyl-amides derived from dextrin are used as the starting polysaccharide.

21. The method according to claim 1, wherein a total ester of the acidic polysaccharide is used as the starting polysaccharide.

22. The method according to claim 1, wherein a partial ester of the acidic polysaccharide is used as the starting polysaccharide.

23. The method according to claim 22, wherein the ester is used in the form of one of its metal or organic base salts.

24. The method according to claim 23, wherein the salt is an alkali metal or alkaline earth salt.

25. The method according to claim 23, wherein the salt is the sodium, potassium or ammonium salt.

26. The method according to claim 23, wherein a salt of a therapeutically acceptable organic base is used.

27. The method according to claim 23, wherein a salt of a pharmacologically inactive base is used.

28. The method according to claim 23, wherein a salt of a pharmacologically active base which has an action that is compatible with the anti-ulcer and gastroprotective action of said choline ester is used.

29. The method according to claim 28, wherein the base itself has anti-ulcer or gastroprotective activity.

30. The method according to claim 1, wherein a choline salt is used as the starting polysaccharide.

* * * * *